United States Patent [19]
Sakai

[11] Patent Number: 5,586,552
[45] Date of Patent: Dec. 24, 1996

[54] PHYSICAL-INFORMATION DETECTING SYSTEM

[75] Inventor: Hiroshi Sakai, Komaki, Japan

[73] Assignee: Colin Corporation, Komaki, Japan

[21] Appl. No.: 341,989

[22] Filed: Nov. 16, 1994

[30] Foreign Application Priority Data

Nov. 29, 1993 [JP] Japan .................................. 5-298385

[51] Int. Cl.⁶ ...................................................... A61B 5/00
[52] U.S. Cl. .......................... 128/633; 128/680; 128/677; 128/681; 128/696; 128/687; 128/903
[58] Field of Search ..................... 128/630, 632, 128/633, 668, 672, 675, 680–3, 677, 687, 691, 670, 671, 695, 700, 701, 716, 736, 748, 903, 904

[56] References Cited

U.S. PATENT DOCUMENTS

| | | |
|---|---|---|
| 3,572,316 | 3/1971 | Vogelman et al. . |
| 5,050,613 | 9/1991 | Newman et al. ....................... 128/676 |
| 5,131,391 | 7/1992 | Sakai et al. . |
| 5,131,400 | 7/1992 | Harada et al. . |
| 5,152,296 | 10/1992 | Simons ................................... 128/633 |
| 5,179,956 | 1/1993 | Harada et al. . |
| 5,309,908 | 5/1994 | Friedman et al. ....................... 128/633 |

FOREIGN PATENT DOCUMENTS

| | | |
|---|---|---|
| 3525014 | 1/1987 | Germany . |
| 53-26437 | 8/1978 | Japan . |
| 61-78453 | 5/1986 | Japan . |
| 62-250728 | 10/1987 | Japan . |
| 1-288289 | 11/1989 | Japan . |
| 2-111343 | 4/1990 | Japan . |
| 2003276 | 3/1979 | United Kingdom . |

Primary Examiner—Angela D. Sykes
Assistant Examiner—Robert L. Nasser
Attorney, Agent, or Firm—Oliff & Berridge

[57] ABSTRACT

A physical-information detecting system including a first detector which detects a first physical information of a first living subject and generates a first physical-information (PI) signal representing the detected first physical information; a second detector which detects a second physical information of a second living subject and generates a second PI signal representing the detected second physical information; a first transmitter which transmits the first PI signal and a first identification (ID) signal identifying the first detector; a second transmitter which transmits the second PI signal and a second ID signal identifying the second detector; a physical-information output device which receives the first and second PI signals and said first and second ID signals from the first and second transmitters and outputs the detected first and second physical information represented by the first and second PI signals; a determining device for determining a characteristic of change of each of the first and second PI signals; and a judging device for judging whether the first and second living subjects are identical with each other, based on the respective determined characteristics of the first and second PI signals, the judging device providing a positive judgment when the respective determined characteristics are substantially identical with each other.

19 Claims, 3 Drawing Sheets

PHYSICAL-INFORMATION DETECTING SYSTEM

BACKGROUND OF THE INVENTION

1. Field of the Invention

The present invention relates to a physical-information detecting system which obtains physical information from a living subject such as a patient.

2. Related Art Statement

A plurality of physiological- or physical-information detecting devices such as an electrocardiograph (ECG), a blood pressure (BP) measuring device (e.g., BP monitor), and/or a blood oxygen saturation measuring device (i.e., oximeter) are used by being worn on each of a plurality of patients, so as to obtain an electrocardiogram, a blood pressure value, and/or a blood oxygen saturation value from the patient, respectively. The thus obtained various sorts of physical information are processed by a common physical-information output device, so that a visual representation of the various sorts of physical information is output for each patient on a display or a record sheet and so that a medical worker observes the plural sorts of physical information all at once.

For example, a group of an ECG, a BP monitor, and an oximeter are worn on each of patients undergoing medical treatments in an intensive care unit (ICU) of a hospital, and three sorts of physical information are transmitted by radio, by optical communication, or alternatively by using respective electric signals from the three detectors to a center display device, so that the display device displays the plural sorts of physical information for each patient, separately from those for the other patients. With this monitor system, a medical worker such as a doctor or a nurse can read the plural sorts of physical information for each patient all at once.

Each of the physical-information detectors generates a physical-information signal representing detected physical information, and an identification signal identifying the particular detector which provides that physical-information signal. The common output device processes the physical-information signal transmitted from each detector, and outputs a visual representation of the physical information represented by the processed signal.

However, if one of the physical-information detectors is erroneously worn on an incorrect patient who is, for example, next to a correct patient to be monitored, the above-indicated, prior physical-information monitor system would output the physical information erroneously obtained from the incorrect patient, as the physical information of the correct patient to be monitored, because the prior monitor system does not identify each patient but only identifies each detector based on the identification signal supplied together with the physical-information signal from that particular detector.

SUMMARY OF THE INVENTION

It is therefore an object of the present invention to provide a physical-information detecting system which includes a plurality of physical-information detectors and which judges whether or not the plurality of physical-information detectors are being worn on one and same living subject.

The above object has been achieved by the present invention, which provides a physical-information detecting system comprising (a) a first detector which detects a first physical information of a living subject and generates a first physical-information signal representing the detected first physical information, (b) a second detector which detects the physical information of a second living subject and generates a second physical-information signal representing the detected second physical information, (c) a first transmitter which transmits the first physical-information signal, and a first identification signal identifying the first detector, (d) a second transmitter which transmits the second physical-information signal, and a second identification signal identifying the second detector, (e) a physical-information output device which receives the first and second physical-information signals and the first and second identification signals, from the first and second transmitters, and outputs the detected first physical information represented by the first physical-information signal and the detected second physical information represented by the second physical-information signal, (f) determining means for determining a characteristic of change of each of the first and second physical-information signals; and (g) judging means for judging whether the detectors are located on the same living subject, based on the respective determined characteristics of the first and second physical-information signals, the judging means providing a positive judgment when the respective determined characteristics are substantially identical with each other.

In the physical-information detecting system constructed as described above, the determining means determines a characteristic of change of each of the first and second physical-information signals, and the judging means provides a positive judgment that the detectors are located on the same living subject are identical with each other, if the respective determined characteristics are substantially identical with each other. On the other hand, if the judging means provides a negative judgment, it means that the first and second detectors are not worn one and same living subject. In this case, the two detectors are worn on the two different subjects, respectively. The two detectors may be either ones which detect a same sort of physical information, or ones which detect different sorts of physical information, respectively.

In a preferred embodiment in accordance with the present invention, the detecting system further comprises an alarm output device which outputs, when the judging means provides a negative judgment, an alarm indicating that detectors are worn on the first and second subjects who are different from each other. In this case, a medical worker can quickly re-arrange the two detectors on a correct subject to be monitored.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
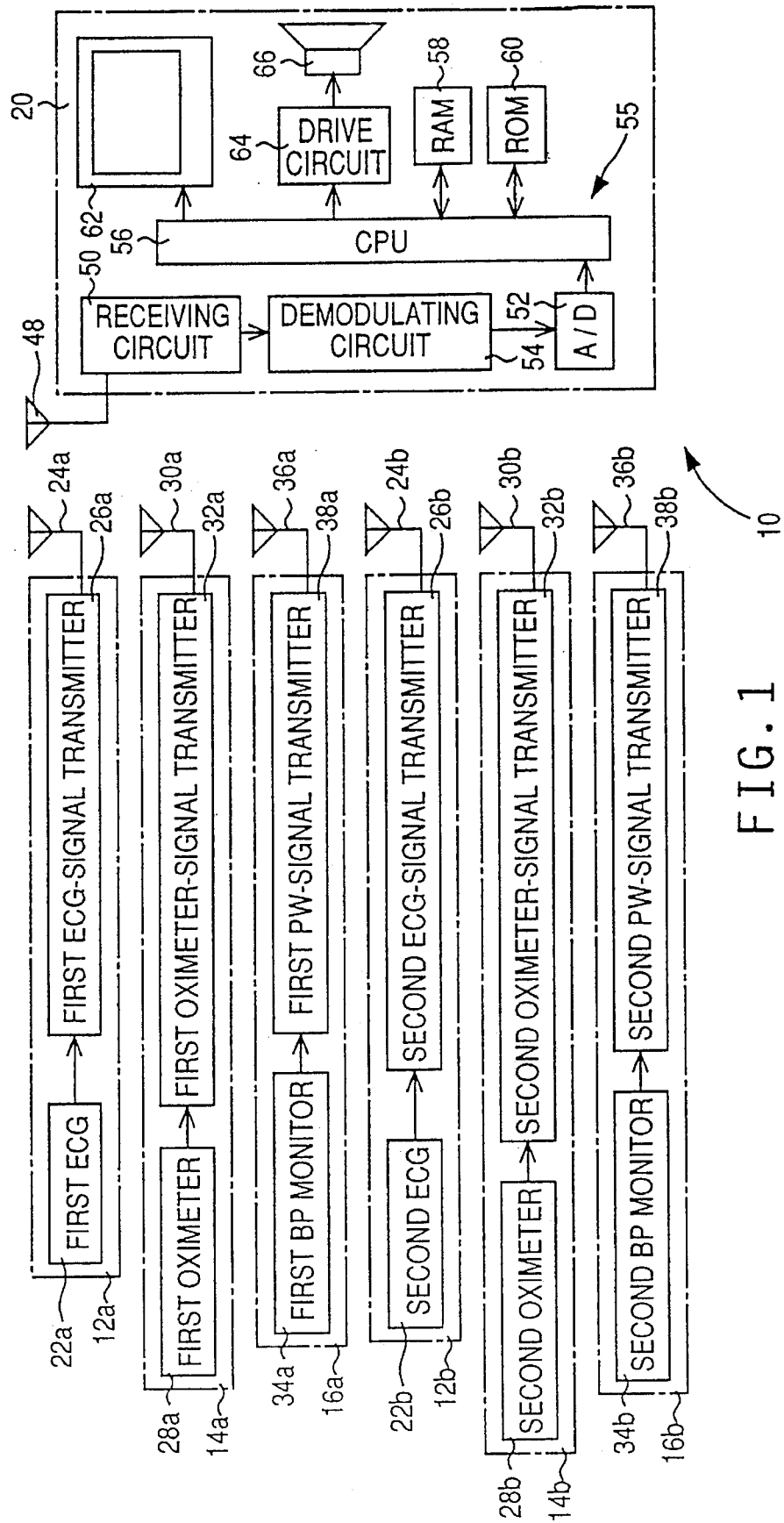
FIG. 1 is a diagrammatic view of a physical-information monitor system to which the present invention is applied.

Referring to FIG. 1, there is shown a physical-information monitor system 10 to which the present invention is applied.

The monitor system 10 includes two or more groups of physical-information detecting and transmitting devices 12 (12a, 12b, ...), 14 (14a, 14b, ...), 16 (16a, 16b, ...) for two or more patients A, B, .... More specifically described, the monitor system 10 includes a first electrocardiograph (ECG) device 12a, a first oximeter device (i.e., blood oxygen saturation measuring device) 14a, and a first blood pressure (BP) monitor device 16a for a first patient A, and includes a second ECG device 12b, a second oximeter device 14b, and a second BP monitor device 16b for a second patient B. The following description relates to the case where the monitor system 10 includes two groups of three physical-information detecting and transmitting devices 12 (12a, 12b), 14 (14a, 14b), 16 (16a, 16b) for two patients A and B. However, the monitor system 10 may be modified to include three or more groups of two, four, or more physical-information detecting and transmitting devices for three or more patients.

The first group of three physical-information detecting and transmitting devices 12a, 14a, 16a are worn on the patient A and detect three sorts of physical information from the patient A. Each of the three individual devices 12a, 14a, 16a transmits a physical-information signal representing a corresponding one of the three sorts of physical information. Similarly, the second group of three physical-information detecting and transmitting devices 12b, 14b, 16b are worn on the patient B and detect the three, same sorts of physical information from the patient B. Each of the three individual devices 12b, 14b, 16b transmits a physical-information signal representing a corresponding one of the three sorts of physical information.

The present monitor system 10 further includes a physical-information receiving and output device 20 which receives the physical-information signal from each of the six physical-information detecting and transmitting devices 12a, 14a, 16a, 12b, 14b, 16b of the first and second groups for the two patients A, B. The receiving and output device 20 processes the received physical-information signals, and displays and records the three sorts of physical-information for each of the two patients A, B separately from each other.

The constructions and functions of the first and second ECG devices 12a, 12b are identical with each other. Each ECG device 12a, 12b includes (a) an electrocardiograph (ECG) 22a, 22b which continuously obtains an electrocardiogram (ECG) through electrodes (not shown) attached to a corresponding patient A, B; and (b) an ECG-signal transmitter 26a, 26b which modulates an ECG signal representing the detected ECG, at a prescribed carrier frequency, and transmits the modulated ECG signal via a radio antenna 24a, 24b. The ECG signal has a waveform including a series of pulses corresponding to a series of heartbeats of the patient A, B.

The constructions and functions of the first and second oximeter devices 14a, 14b are identical with each other. Each oximeter device 14a, 14b includes (a) an oximeter 28a, 28b which includes (a1) a transmission-type or reflection-type probe (not shown) for continuously emitting two lights having different frequencies toward the skin of a corresponding patient A, B and continuously detecting intensities of each of the two lights transmitted through, or reflected from, the skin of the patient A, B, (a2) a calculator (not shown) for successively determining blood oxygen saturation values of the patient A, B based on the continuously detected intensities of each of the two lights, and (a3) a signal generator for generating an oximeter signal including the waveform of the continuously detected intensities of each of the two lights and the successively determined blood oxygen saturation values; and (b) an oximeter-signal transmitter 32a, 32b which modulates the oximeter signal at a prescribed carrier frequency and transmits the modulated oximeter signal via a radio antenna 30a, 30b. Each of the respective waveforms of the continuously detected intensities of the two lights includes a series of pulses corresponding to a series of heartbeats of the patient A, B. The above-indicated transmission-type probe is disclosed in Examined Japanese Patent Application laid open for opposition under Publication No. 53(1978)-26437, and the reflection-type probe is disclosed in U.S. Pat. No. 5,131,391 or Unexamined Japanese Patent Application laid open under Publication No. 2(1990)-111343. The above-indicated calculator determines the blood oxygen saturation values according to the calculation method disclosed in the above indicated Japanese documents or U.S. document.

The constructions and functions of the first and second BP monitor devices 16a, 16b are identical with each other. Each BP monitor device 16a, 16b includes (a) a blood pressure (BP) monitor 34a, 34b which includes (a1) a pulse wave (PW) detector probe (not shown) whose press surface, in which an array of pressure sensing elements are provided, is adapted to be pressed against an artery under the skin of a corresponding patient A, B and (a2) a control device (not shown) for controlling the pressing force applied to the PW detector probe and thereby continuously obtaining a pulse wave (PW) signal representing the intra-arterial pressure of the artery, i.e., blood pressure of the patient A, B, through each of the pressure sensing elements; and (b) a PW-signal transmitter 38a, 38b which modulates the PW signal at a prescribed carrier frequency and transmits the modulated PW signal via a radio antenna 36a, 36b. The PW signal has a waveform including a series of pulses corresponding to a series of heartbeats of the patient A, B. The above-indicated PW detector probe is disclosed in U.S. Pat. No. 5,131,400 or U.S. Pat. No. 5,179,956. The above-indicated control device operates according to the control method disclosed in Unexamined Japanese Patent Application laid open under Publication No. 1(1989)-288289.

Each of the six signal transmitters 26a, 26b, 32a, 32b, 38a, 38b modulates a 16-bit code signal as a corresponding physical-information signal, and transmits the modulated signal together with a device identification code or signal identifying a corresponding detecting and transmitting device 12a, 12b, 14a, 14b, 16a, 16b which transmits the above-indicated corresponding physical-information signal, and together with an information identification code or signal identifying the particular sort of the corresponding physical-information signal, i.e., one of the ECG, oximeter, and PW signals.

The physical-information receiving and output device 20 includes a receiving circuit 50 which receives, via a radio antenna 48, the physical-information signals supplied from the respective signal transmitters 26a, 26b, 32a, 32b, 38a, 38b of the six detecting and transmitting devices 12a, 12b, 14a, 14b, 16a, 16b. The receiving and output device 20 further includes a demodulating circuit 54 which separates the six physical-information signals received by the receiving circuit 50, from each other, based on the respective device and information identification signals received together with the physical-information signals. The demodulating circuit 54 outputs the thus separated physical-information signals via an analog-to-digital (A/D) converter 52 to a control device 55 including a microcomputer comprised of a central processing unit (CPU) 56, a random access memory (RAM) 58, and a read only memory (ROM) 60. The CPU 56 processes the input signals according to control programs pre-stored in the ROM 60 by utilizing a temporary-storage function of the RAM 58. More specifically described, the CPU 56 processes the two ECG signals, the two oximeter signals, and the two PW signals, and operates an output device 62 to display, on a screen thereof, the ECG waveform, blood oxygen saturation values in digits, and waveform of intra-arterial blood pressure of each of the two patients A, B, separately from each other. In addition, the CPU 56 determines a characteristic of change of each of the ECG, oximeter, and PW signals supplied from each group of physical-information detecting and transmitting devices, i.e., first group 12a, 14a, 16a or second group 12b, 14b, 16b, and compares the thus obtained three characteristics (i.e., evaluated values) with one another. If the comparison results indicate that one of the three characteristics is different from the other two characteristics, the CPU 56 operates a drive circuit 64 to drive a speaker 66 so as to output an alarm sound indicating that the three detecting and transmitting devices of the group (12a, 14a, 16a), (12b, 14b, 16b) in question are not worn on the one and same patient A or B but worn on the two patients A and B. In the present embodiment, the output of an alarm sound means that the three detecting and transmitting devices of the first group 12a, 14a, 16a are misarranged with those 12b, 14b, 16b of the second group, on the two patients A, B.

The physical-information receiving and output device 20 functions as characteristic determining means for determining a characteristic of change of the magnitudes of each of the ECG, oximeter, and PW signals supplied from each group (12a, 14a, 16a), (12b, 14b, 16b), by, e.g., determining the period of pulsation of each signal which corresponds to the period of heartbeat of a corresponding patient A, B, and also functions as judging means for judging whether the three detecting and transmitting devices of each group (12a, 14a, 16a), (12b, 14b, 16b) are worn on the one and same patient A or B, based on the determined periods of pulsation of the three signals supplied from each group (12a, 14a, 16a), (12b, 14b, 16b). In the case where the three detecting and transmitting devices of each group (12a, 14a, 16a), (12b, 14b, 16b) are worn on the one and same patient A or B, the respective periods of pulsation of the three signals supplied from each group (12a, 14a, 16a), (12b, 14b, 16b) must be substantially equal to one another. Therefore, if one of the three periods of pulsation is different from the other two periods of pulsation, the judging means provides a negative judgment. In this case, a medical worker such as a doctor or a nurse needs to re-arrange the detecting and transmitting devices of the group (12a, 14a, 16a), (12b, 14b, 16b) in question and properly puts those devices on an appropriate patient A or B.

Hereinafter, there will be described the operation of the physical-information monitor system 10 constructed as described above, by reference to the flow chart of FIG. 2.

First, at Step S1, the CPU 56 of the control device 55 reads in the six physical-information signals and the respective device and information identification signals which have been received by the receiving circuit 50 and demodulated by the demodulating circuit 54. Step S1 is followed by Step S2 to class the six physical-information signals into a first signal group, $G_A$, consisting of the ECG, oximeter, and PW signals for the patient A, and a second signal group, $G_B$, consisting of the ECG, oximeter, and PW signals for the patient B, based on the respective device and information identification signals associated with the six physical-information signals. The CPU 56 records the two signal groups $G_A$, $G_B$ in RAM 58, separately from each other.

At the following Step S3, the CPU 56 evaluates a characteristic of change of each of the ECG, oximeter, and PW signals of each signal group $G_A$, $G_B$. In the present embodiment, the CPU 56 determines a period, $T_{ECGA}$, of pulsation of the ECG signal, a period, $T_{OXIA}$, of pulsation of the oximeter signal, and a period, $T_{BPA}$, of pulsation of the PW signal, for the first signal group $G_A$. Similarly, the CPU 56 determines a period, $T_{ECGB}$, of pulsation of the ECG signal, a period, $T_{OXIB}$, of pulsation of the oximeter signal, and a period, $T_{BPB}$, of pulsation of the PW signal, for the second signal group $G_B$.

Step S3 is followed by Step S4 to judge whether the three evaluated characteristics of each signal group $G_A$, $G_B$ are substantially equal to one another. In the present embodiment, the CPU 56 judges whether the three determined periods $T_{ECGA}$, $T_{OXIA}$, $T_{BPA}$, of the first signal group $G_A$ are substantially equal to one another and simultaneously judges whether the three determined periods $T_{ECGB}$, $T_{OXIB}$, $T_{BPB}$, of the second signal group $G_B$ are substantially equal to one another.

If a positive judgment is made at Step S4, the control of the CPU 56 proceeds with Step S5 to operate the output device 62 to display and record, based on the first signal group $G_A$ for the patient A, (A) the ECG waveform represented by the ECG signal of the group $G_A$, (B) (b1) a curve representing the time-wise change of the blood oxygen saturation values and (b2) a current blood oxygen saturation value represented by the oximeter signal, and (C) (c1) the waveform of intra-arterial blood pressure represented by the PW signal and (c2) current systolic and diastolic blood pressure values corresponding to the upper and lower peaks of each pulse of the PW signal. Simultaneously, the output device 62 displays and records the same sorts of physical information for the patient B, based on the second signal group $G_B$, separately from those for the patient A.

On the other hand, if a negative judgment is made at Step S4, the control of the CPU 56 goes to Step S6 to output alarms indicating that the three evaluated characteristics of each signal group $G_A$, $G_B$ are not equal to one another. For example, in the case where one of the three determined periods $T_{ECGA}$, $T_{OXIA}$, $T_{BPA}$, for the patient A is different from the other two determined periods, the CPU 56 controls the output device 62 to display a visual alarm message specifying the particular detecting device 12a, 14a, 16a which has provided that one period different from the other two periods substantially equal to each other, and controls the display 62 to stop displaying all the sorts of physical information for the patient A. Alternatively, in this case, it is possible to stop displaying only the particular sort of physical information supplied from the particular detecting device 12a, 14a, 16a which has provided the different period. Simultaneously, the CPU 56 controls the drive circuit 64 and the speaker 66 to output a sound alarm message specifying the particular detecting device 12a, 14a, 16a which has erroneously been worn on a patient other than the patient A. Furthermore, in the case where all the three evaluated characteristics of each signal group $G_A$, $G_B$ are different from one another, the CPU 56 operates the display 62 and the speaker 66 to output a visual and a sound alarm message each informing the medical worker of that erroneous wearing of the three detecting devices of a corresponding group (12a, 14a, 16a), (12b, 14b, 16b).

In the present embodiment, Step S3 and a portion of the control device 56, 58, 60 for carrying out Step S3 function as characteristic determining means for determining the period $T_{ECG}$ of pulsation of the ECG signal, the period $T_{OXI}$ of pulsation of the oximeter signal, and the period $T_{BP}$ of pulsation of the PW signal, for each signal group $G_A$, $G_B$, and Step S4 and a portion of the control device 56, 58, 60 for carrying out Step S4 function as judging means for judging whether the three determined periods $T_{ECG}$, $T_{OXI}$, $T_{BP}$ for each patient A, B are substantially equal to each other. If the judging means identifies that one of the three determined periods $T_{ECG}$, $T_{OXI}$, $T_{BP}$ for each patient A, B is different from the other two determined periods substantially equal to each other, the CPU 56 identifies the particular detecting device 12 (12a, 12b), 14 (14a, 14b), 16 (16a, 16b) which has provided that one period different from the other two periods and judges that the thus identified particular detecting device 12, 14, 16 has erroneously been worn on the patient A, B. Thus, the present monitor system 10 ensures that a medical worker makes a correct decision and takes a quick action on each patient A, B by observing the physical sorts of information obtained from the patient A, B by the present system 10.

Figure 3:
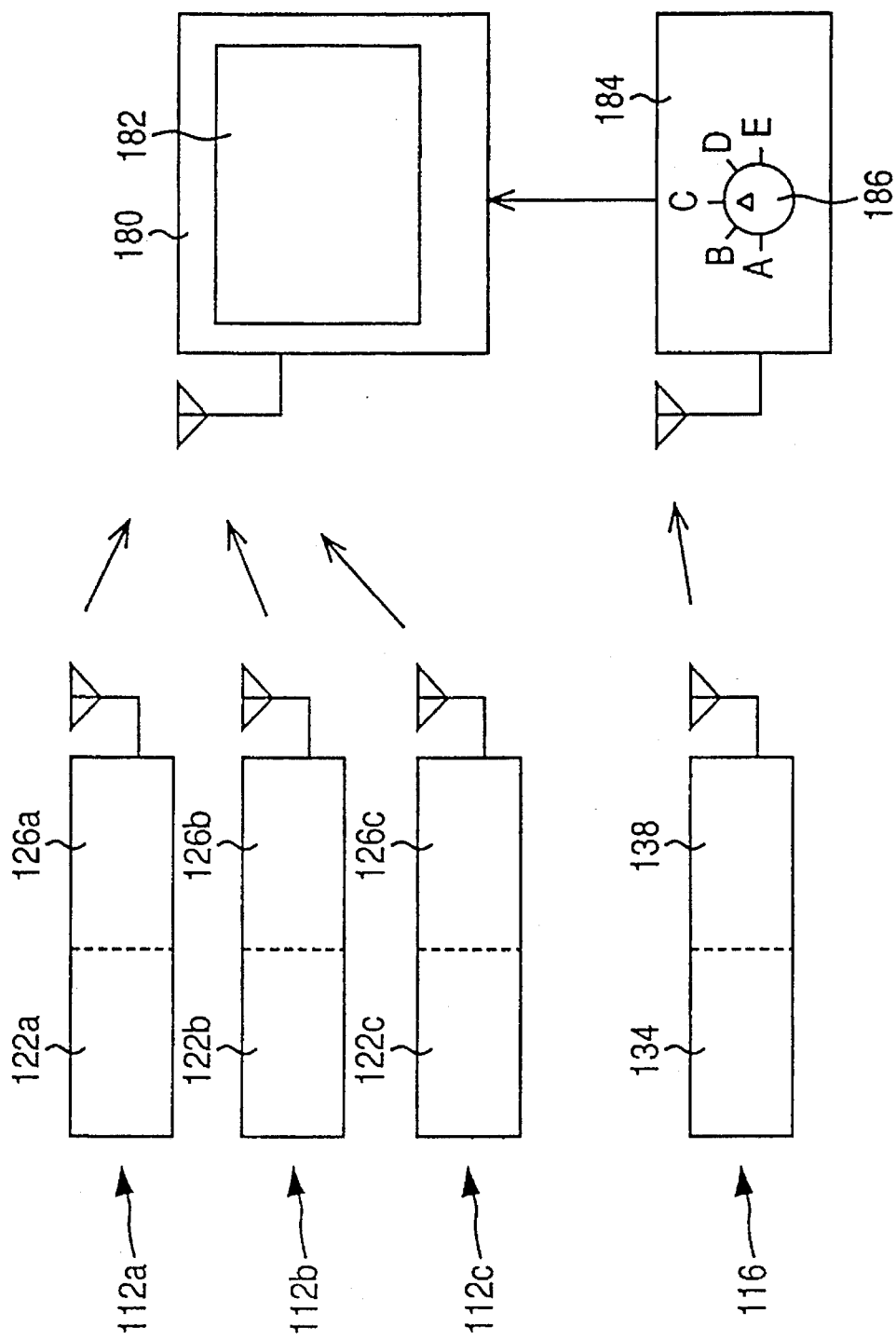
FIG. 3 is a diagrammatic view corresponding to FIG. 1, illustrating another physical-information monitor system as a second embodiment of the present invention.

Referring next to FIG. 3, there is shown a second embodiment of the present invention. The second embodiment relates to a physical-information monitor system 100.

A first, a second, and a third electrocardiograph (ECG) device 112a, 112b, 112c are worn on three patients A, B, C, respectively. The ECG devices 112a, 112b, 112c are identical with the ECG devices 12a, 12b shown in FIG. 1, and each ECG device 112a, 112b, 112c includes an ECG 122a, 122b, 122c and an ECG-signal transmitter 126a, 126b, 126c. Each of the ECG devices 112a, 112b, 112c transmits, by radio, an ECG signal to a monitor device 180. The monitor device 180 receives the ECG signal from each ECG device 112a, 112b, 112c and demodulates the received ECG signals. The monitor device 180 includes a screen 182 and displays, on the screen 182, the waveform or electrocardiogram (ECG) represented by the demodulated ECG signal for each of the patients A, B, C, separately from one another.

A blood pressure (BP) monitor device 116 is worn, as needed, on one of the patents A, B, C. The BP monitor device 116 includes a BP monitor 134 and a PW-signal transmitter 138. In the present embodiment, the BP monitor device 116 employs a signal coding and transmitting techniques different from those employed by the ECG devices 112a, 112b, 112c, because the BP monitor device 116 and the ECG devices 112a, 112b, 112c may have been produced by different manufacturers, respectively. Therefore, the monitor device 180 either cannot directly receive the ECG signals transmitted from the ECG devices 112a, 112b, 112c or, even if the monitor device 180 may receive the ECG signals, the received ECG signal may be too poor and therefore may not be used. Hence, in the present embodiment, the monitor system 100 further includes a signal receiving device 184 which has been produced by the same manufacturer as that for the BP monitor device 116 and which can receive, demodulate, and process a pulse wave (PW) signal transmitted from the BP monitor device 116.

The signal receiving device 184 has a select dial 186 which is operable or turnable by a medical worker for selecting one of the patients A, B, C (and additionally patients D and/or E, when appropriate) on whom the BP monitor device 116 has been worn or will be worn. The signal receiving device 184 receives the PW signal from the BP monitor device 116, processes the received PW signal into the waveform of intra-arterial blood pressure, and generates a BP digital signal representing the intra-arterial blood pressure (BP) waveform. The signal receiving device 184 also generates a patient (or bed) identification code or signal identifying a selected one patient A, B, C who is currently specified by the select dial 186 and on whom the BP monitor device 116 is currently set. The BP digital signal and patient identification signal generated by the signal receiving device 184 are compatible with a signal decoding technique employed by the monitor device 180.

Figure 2:
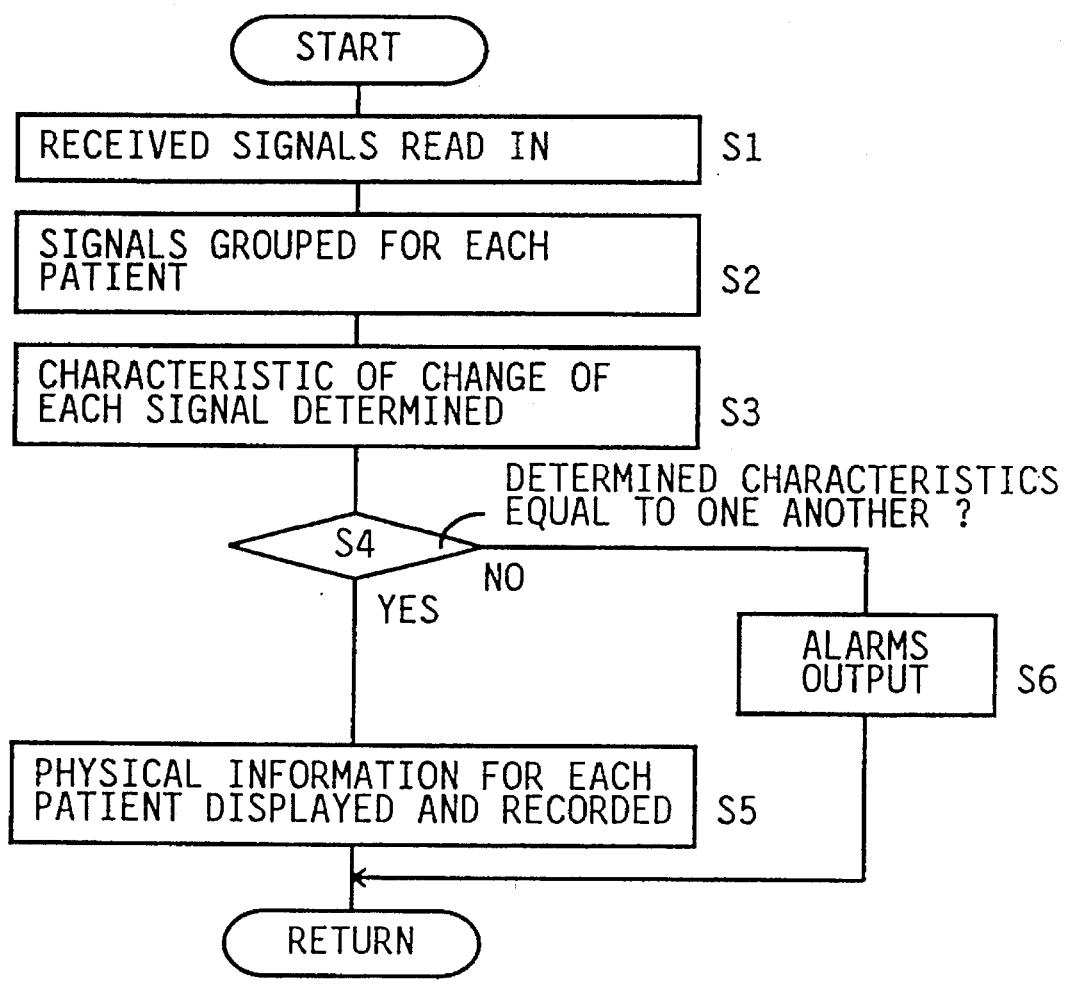
FIG. 2 is a flow chart representing a control program according to which the monitor system of FIG. 1 operates.

The present monitor system 100 operates according to the control program represented by the flow chart of FIG. 2, not for all the patients A, B, C but for only a selected one patient A, B, C who is currently specified by the select dial 186 and on whom the BP monitor device 116 is currently worn. More specifically, at Step S1, a CPU (not shown) of the monitor device 180 reads in the ECG signal supplied from one ECG device 112a, 112b, 112c worn on the selected patient A, B, C, and then at Step S2 the CPU associates the ECG signal with the BP digital signal supplied from the signal receiving device 184, based on the patient identification signal supplied from the signal receiving device 184 associated with the BP digital signal. At the following Step S3, the CPU determines a period, $T_{ECG}$, of pulsation of the ECG waveform represented by the ECG signal, and a period, $T_{BP}$, of pulsation of the BP waveform represented by the BP digital signal. Subsequently, at Step S4, the CPU judges whether the two periods $T_{ECG}$, $T_{BP}$ are substantially equal to each other. If a negative judgment is made at Step S4, the control of the CPU goes to Step S6 to display, on the screen 182 of the monitor device 180, a visual alarm message indicating that the patient currently specified by the select dial 186 is different from the patient currently wearing the BP monitor device 116. In addition, the CPU controls a sound output device (not shown) of the monitor device 180 to output a sound alarm message indicating the same.

Also in the second embodiment, it is judged whether the respective characteristics of change of a plurality of sorts of physical information relating to a particular patient are substantially equal to each other. A negative judgment indicates either that the BP monitor device 116 has been worn on a patient different from the particular patient or that the select dial 186 has been turned to specify a patient different from that particular patient. Thus, the present monitor system 100 ensures that a medical worker makes a correct decision and takes a quick action on each patient A, B, C by observing the sorts of physical information obtained from the patient A, B, C by the present system 10.

While the present invention has been described in its preferred embodiments, the invention may otherwise be embodied.

For example, in the illustrated embodiments, the respective periods of pulsation of the ECG, oximeter, and PW (or BP) signals each corresponding to the period of heartbeat of each patient A, B are determined as the respective characteristics of change of a plurality of sorts of physical information. However, the respective waveforms of continuously detected intensities of the two lights represented by the oximeter signal, and the waveform of continuously detected intra-arterial blood pressure values represented by the PW signal, each include a component changeable in synchronism with respiration of each patient A, B. In the case where the oximeter devices 28 and the BP monitor devices 34 are used, the respective periods of change of the oximeter and PW signals each corresponding to the period of respiration of each patient A, B may be determined as the respective characteristics of change of a plurality of sorts of physical information, so as to identify whether the oximeter and PW signals are being obtained from one and same patient A or B.

In addition, the respective amplitudes of successive pulses of each of the ECG-signal, oximeter-signal, and PW-signal waveforms obtained from one and same patient A, B must change similarly to each other. Therefore, the tendency of change (e.g., rate of change) of successively determined amplitudes of each of those signal waveforms may be determined as the characteristic of change of each of a plurality of sorts of physical information.

For the same reason, the tendency of change (e.g., rates of change) of successively determined pulsation periods of each of the ECG-signal, oximeter-signal, and PW-signal waveforms may be determined as the characteristic of change of each of a plurality of sorts of physical information.

Although in the illustrated embodiments the radio waves transmitted from the signal transmitters 26, 32, 38, 126, 138 are received by the signal receiving and output device 20 or monitor device 180 via a radio antenna and a receiving circuit, the ECG, oximeter, or PW signal may be transmitted from each detector device 12, 14, 16, 112, 116 to the monitor device 20, 180, alternatively via a known signal cable, by optical communication as disclosed in Unexamined Japanese Utility Model Application laid open under Publication No. 61-78453, or via an electric-power line as disclosed in Unexamined Japanese Patent Application laid open under Publication No. 62-250728.

While in the illustrated embodiments the respective characteristics of change of a plurality of sorts of physical information are determined by the signal receiving and output device 20 or monitor device 180, it is possible to modify the ECG devices 12, 112, oximeter devices 14, and BP monitor devices 16, 116 so that the ECGs 22 (22a, 22b, ...) or 122 (122a, 122b, 122c, ...), oximeters 28 (28a, 28b, ...), and BP monitors 34 (34a, 34b, ...) or 116 each determine the respective periods $T_{ECG}$, $T_{OXI}$, $T_{BP}$ of the ECG, oximeter, and PW signals, and each of the signal transmitters 26 (26a, 26b, ...) or 126 (126a, 126b, 126c, ...), 32 (32a, 32b, ...), 38 (38a, 38b, ...) or 138 transmits, to the monitor device 20, 180, a corresponding one of the periods $T_{ECG}$, $T_{OXI}$, $T_{BP}$ together with a corresponding one of the ECG, oximeter, and PW signals.

Although in the first embodiment the oximeter devices 14 (14a, 14b, ...) calculate the blood oxygen saturation values, it is possible to adapt the oximeter devices 14 so that each of the oximeters 28 (28a, 28b, ...) obtains the respective waveforms of continuously detected intensities of the two transmitted or reflected lights having different frequencies and each of the oximeter-signal transmitters 32 (32a, 32b, ...) transmits a waveform signal representing only the respective waveforms of continuously detected intensities of the two lights. In this case, the signal receiving and output device 20 is modified to successively calculate blood oxygen saturation values based on the respective waveforms of continuously detected intensities of the two lights represented by the received waveform signal.

While in the illustrated embodiments the ECG devices 12, 112, oximeter devices 14, and BP monitor devices 16, 116 are employed as the physical-information detecting devices, it is possible to employ an expired-gas sensor, a carbonic-acid-gas sensor, and/or an invasive blood pressure measuring device using a catheter, all of which may be used on a patient undergoing a surgical operation, in addition to, or in place of, the illustrated devices 12, 112, 14, 16, 116.

It is to be understood that the present invention may be embodied with other changes, modifications, and improvements that may occur to those skilled in the art without departing from the scope and spirit of the invention defined in the appended claims.

What is claimed is:

1. A physical-information detecting system comprising:

a first detector which detects a first physical information of a living subject and generates a first physical-information signal representing the detected first physical information;

a second detector which detects a second physical information of said living subject and generates a second physical-information signal representing the detected second physical information;

a first transmitter which transmits said first physical-information signal, and a first identification signal identifying said first detector;

a second transmitter which transmits said second physical-information signal, and a second identification signal identifying said second detector;

a physical-information output device which receives said first and second physical-information signals and said first and second identification signals, from said first and second transmitters, and outputs said detected first physical information represented by said first physical-information signal and said detected second physical information represented by said second physical-information signal;

determining means for determining a characteristic of change of each of said first and second physical-information signals; and judging means for judging whether said first and second detectors are located on the same living subject based on the respective determined characteristics of said first and second physical-information signals, said judging means providing a positive judgment when said respective determined characteristics are substantially identical with each other.

2. A detecting system according to claim 1, wherein said first and second detectors comprise one of an electrocardiograph, a blood pressure measuring device, and a blood oxygen saturation measuring device.

3. A detecting system according to claim 1, wherein said determining means comprises means for determining, as said characteristic of change of said each of said first and second physical-information signals, a period of pulsation of said each physical-information signal that is equal to a period of heartbeat of said living subject, said judging means providing said positive judgment when the respective determined pulsation periods of said first and second physical-information signals are substantially equal to each other.

4. A detecting system according to claim 1, wherein said first detector detects, as said first physical information, a first sort of physical information of said living subject, and said second detector detects, as said second physical information, a second sort of physical information of said living subject, said first and second sorts being different from each other.

5. A detecting system according to claim 4, further comprising:

a third detector which detects a third sort of physical information of said living subject and generates a third physical-information signal representing the detected third physical information, said third sort being different from said first and second sorts; and a third transmitter which transmits said third physical-information signal, and a third identification signal identifying said third detector, said physical-information output device receiving said third physical-information signal and said third identification signal from said third transmitter and outputs said detected third physical information represented by said third physical-information signal, said determining means determining a characteristic of change of said third physical-information signal, said judging means judging whether said first, second, and third detectors are located on the same living subject, based on the respective determined characteristics of said first, second, and third physical-information signals, said judging means providing a positive judgment when said respective determined characteristics of said first, second, and third physical-information signals are substantially identical with one another.

6. A detecting system according to claim 5, wherein said first, second, and third detectors comprise a first, a second, and a third one of an electrocardiograph, a blood pressure measuring device, and a blood oxygen saturation measuring device, respectively.

7. A detecting system according to claim 5, wherein said judging means comprises means for judging that each of said first, second, and third detectors is located on a different living subject, different from said living subject, when a corresponding one of said respective determined characteristics of said first, second, and third physical-information signals is different from the other determined characteristics.

8. A detecting system according to claim 7, further comprising an informing device which informs an operator of which one of said first, second, and third detectors is judged as being located on said different living subject.

9. A detecting system according to claim 7, further comprising a control device which controls said physical-information output device to stop outputting one of said first, second, and third physical information which corresponds to said each of said first, second and third detectors judged as being located on said different living subject.

10. A detecting system according to claim 4, further comprising:

a third detector which detects a third sort of physical information of said living subject and generates a third physical-information signal representing the detected third physical information, said third sort being the same as said first sort and different from said second sort;

a fourth detector which detects a fourth sort of physical information of said living subject and generates a fourth physical-information signal representing the detected fourth physical information, said fourth sort being different from said first sort and the same as said second sort;

a third transmitter which transmits said third physical-information signal, and a third identification signal identifying said third detector; and a fourth transmitter which transmits said fourth physical-information signal, and a fourth identification signal identifying said fourth detector, said physical-information output device receiving said third and fourth physical-information signals and said third and fourth identification signals, from said third and fourth transmitters, and outputting, separately from a first group of said detected first and second physical information represented by said first and second physical-information signals, a second group of said detected third physical information represented by said third physical-information signal and said detected fourth physical information represented by said fourth physical-information signal based on said first, second, third, and fourth identification signals, said determining means determining a characteristic of change of each of said third and fourth physical-information signals, said judging means judging whether said third and fourth detectors are located on the same living subject, based on the respective determined characteristics of said third and fourth physical-information signals, said judging means providing a positive judgment when said respective determined characteristics of said third and fourth physical-information signals are substantially identical with each other.

11. A detecting system according to claim 10, further comprising a memory which stores said first group of said detected first and second physical information, and said second group of said detected third and fourth physical information, separately from each other.

12. A detecting system according to claim 1, further comprising an alarm output device which outputs, when said judging means makes a negative judgment, an alarm indicating that said first and second detectors are worn on said living subject and a different living subject respectively.

13. A detecting system according to claim 12, wherein said alarm output device comprises a sound output device which outputs a sound as said alarm.

14. A detecting system according to claim 12, wherein said alarm output device comprises a display which displays a message as said alarm.

15. A detecting system according to claim 1, further comprising a control device which controls, when said judging means makes a negative judgment, said physical-information output device to stop outputting said detected first and second physical information.

16. A detecting system according to claim 1, further comprising:

a selecting device which is operable for selecting one of said living subject and a different living subject; and a first signal receiver which receives one of said first and second physical-information signals from a corresponding one of said first and second transmitters corresponding to said first and second detectors, respectively, and supplies, to said physical-information output device, the received one physical-information signal and a subject and detector identification signal identifying the selected one living subject and one of said first and second detectors which corresponds to said received one physical-information signal, said physical-information output device receiving said one physical-information signal via said signal receiver from said corresponding one transmitter, and said subject and detector identification signal from said first signal receiver, said physical information output device additionally receiving, from the other of said first and second transmitters which corresponds to the other of said first and second detectors, the other of said first and second physical information signals and one of said first and second identification signals which corresponds to said other physical-information signal, said determining means determining the characteristic of change of said one physical-information signal supplied from said corresponding one transmitter via said first signal receiver, and additionally determining the characteristic of change of said other physical-information signal transmitted from said other transmitter, said judging means providing a positive judgment that said first and second detectors as said one and other detectors are located on the same living subject as said selected one living subject when the respective determined characteristics of said one and other physical-information signals are substantially identical with each other.

17. A detecting system according to claim 16, further comprising an alarm output device which outputs, when said judging means provides a negative judgment, an alarm indicating that said first and second detectors are worn on said living subject and said different living subject, respectively.

18. A detecting system according to claim 1, wherein said physical-information output device comprises at least one of (a) a display which displays said detected first and second physical information represented by said first and second physical-information signals and (b) a recorder which records, on a recording medium, said detected first and second physical information.

19. A detecting system according to claim 1, wherein said first and second transmitters transmit, by radio, said first and second physical-information signals and said first and second identification signals, and said physical-information output device comprises a second signal receiver which receives, by radio, said first and second physical-information signals and said first and second identification signals from said first and second transmitters.

* * * * *